(12) United States Patent
Colby

(10) Patent No.: US 9,422,159 B2
(45) Date of Patent: Aug. 23, 2016

(54) QUANTUM DOT DIGITAL RADIOGRAPHIC DETECTION SYSTEM

(76) Inventor: Leigh E. Colby, Eugene, OR (US)

( * ) Notice: Subject to any disclaimer, the term of this patent is extended or adjusted under 35 U.S.C. 154(b) by 396 days.

(21) Appl. No.: 13/184,469

(22) Filed: Jul. 15, 2011

(65) Prior Publication Data

US 2013/0187053 A1    Jul. 25, 2013

Related U.S. Application Data

(60) Provisional application No. 61/364,448, filed on Jul. 15, 2010.

(51) Int. Cl.
  *G01T 1/20*  (2006.01)
  *B82Y 15/00*  (2011.01)
  *B82Y 20/00*  (2011.01)

(52) U.S. Cl.
  CPC ........ *B82Y 15/00* (2013.01); *B82Y 20/00* (2013.01)

(58) Field of Classification Search
  CPC ... G01T 1/2018; G01T 1/1644; G01T 1/1645; G01T 1/20; G01T 1/2006
  USPC .................................................. 250/370.14
  See application file for complete search history.

(56) References Cited

U.S. PATENT DOCUMENTS

| | | | |
|---|---|---|---|
| 5,017,782 A | | 5/1991 | Nelson |
| 5,753,924 A * | | 5/1998 | Swann ............ 250/443.1 |
| 6,194,726 B1 * | | 2/2001 | Pi et al. ............ 250/363.1 |
| 6,593,589 B1 | | 7/2003 | Osinkski et al. |
| 6,885,004 B2 | | 4/2005 | Taskar et al. |
| 7,019,297 B2 * | | 3/2006 | Aykac et al. ............ 250/368 |
| 7,038,211 B2 | | 5/2006 | Bross et al. |
| 7,067,072 B2 | | 6/2006 | Chen |
| 7,126,136 B2 | | 10/2006 | Chen |
| 7,199,372 B2 | | 4/2007 | Kardynal et al. |
| 7,250,608 B2 | | 7/2007 | Ozeki |
| 7,265,354 B2 * | | 9/2007 | Kastalsky ............ G01T 1/2018  250/370.01 |
| 7,282,713 B2 | | 10/2007 | Jiang et al. |
| 7,294,847 B2 | | 11/2007 | Imai |
| 7,304,309 B2 | | 12/2007 | Suhami |
| 7,538,329 B2 | | 5/2009 | Chen et al. |

(Continued)

FOREIGN PATENT DOCUMENTS

JP        2002040143 A      2/2002

OTHER PUBLICATIONS

Kambe et al., Refractive Index Engineering of nano-poly Composites, Mat. Res. Soc. Symp. Proc. vol. 676 2001.*

(Continued)

*Primary Examiner* — Marcus Taningco
*Assistant Examiner* — Djura Malevic
(74) *Attorney, Agent, or Firm* — Law Office of Karen Dana Oster, LLC

(57) ABSTRACT

A digital quantum dot radiographic detection system described herein includes: a scintillation subsystem and a semiconductor visible light detection subsystem (including a plurality of quantum dot image sensors). In a first preferred digital quantum dot radiographic detection system, the plurality of quantum dot image sensors is in substantially direct contact with the scintillation subsystem. In a second preferred digital quantum dot radiographic detection system, the scintillation subsystem has a plurality of discrete scintillation packets, at least one of the discrete scintillation packets communicating with at least one of the quantum dot image sensors.

31 Claims, 14 Drawing Sheets

(56) References Cited

U.S. PATENT DOCUMENTS

| | | | |
|---|---|---|---|
| 7,608,829 B2 | 10/2009 | Loureiro et al. | |
| 7,643,607 B2 | 1/2010 | Jiang et al. | |
| 7,652,261 B1 | 1/2010 | Wilson et al. | |
| 7,683,340 B2* | 3/2010 | Friedman | 250/385.1 |
| 7,723,687 B2* | 5/2010 | Nagarkar | G01T 1/202 250/361 R |
| 7,750,294 B2 | 7/2010 | Bright et al. | |
| 7,773,404 B2* | 8/2010 | Sargent et al. | 365/129 |
| 7,825,399 B2 | 11/2010 | See et al. | |
| 7,857,993 B2* | 12/2010 | Dai et al. | 252/301.17 |
| 7,902,517 B1 | 3/2011 | Ianakiev et al. | |
| 2002/0039833 A1* | 4/2002 | Bensahel et al. | 438/503 |
| 2002/0092987 A1* | 7/2002 | Cho et al. | 250/338.4 |
| 2004/0012689 A1* | 1/2004 | Tinnerino et al. | 348/218.1 |
| 2004/0232342 A1* | 11/2004 | Aykac et al. | 250/367 |
| 2005/0082543 A1* | 4/2005 | Alizadeh et al. | 257/79 |
| 2005/0139777 A1* | 6/2005 | Rostaing et al. | 250/394 |
| 2007/0085010 A1 | 4/2007 | Letant et al. | |
| 2007/0158551 A1* | 7/2007 | Audebert et al. | 250/306 |
| 2008/0128631 A1 | 6/2008 | Suhami | |
| 2008/0210878 A1* | 9/2008 | Friedman | 250/374 |
| 2008/0224054 A1* | 9/2008 | Lehmann et al. | 250/370.01 |
| 2008/0230704 A1* | 9/2008 | Daghighian | A61B 6/037 250/363.03 |
| 2009/0152530 A1* | 6/2009 | Ahn et al. | 257/24 |
| 2009/0179155 A1 | 7/2009 | Weinberg | |
| 2010/0001209 A1 | 1/2010 | Osinski et al. | |
| 2010/0012846 A1 | 1/2010 | Wang | |
| 2010/0072374 A1 | 3/2010 | Osinski et al. | |
| 2010/0133418 A1* | 6/2010 | Sargent et al. | 250/208.1 |
| 2010/0155616 A1 | 6/2010 | Friedman | |
| 2010/0200758 A1 | 8/2010 | Fukuda et al. | |
| 2010/0309460 A1 | 12/2010 | Sargent et al. | |
| 2010/0320369 A1* | 12/2010 | Koskinen et al. | 250/226 |
| 2011/0024685 A1 | 2/2011 | Clothier et al. | |
| 2012/0002040 A1* | 1/2012 | Roth et al. | 348/135 |
| 2012/0068154 A1 | 3/2012 | Hwang et al. | |
| 2013/0028379 A1 | 1/2013 | Nelson et al. | |

OTHER PUBLICATIONS

Rachel Courtland, "Quantum Dots Get Doped," web article, Apr. 5, 2011, 2 pages, IEEE Spectrum—Semiconductors/Materials.

International Searching Authority, "International Search and Written Opinion" and related documents for PCT/US2013/031813, dated May 31, 2013, 10 pages.

Kambe et al., Refractive Index Engineering of Nano-Polymer Composites, Mat. Res. Soc. Symp. Proc. vol. 676, © 2001 Materials Research Society, at least as early as 2001, 6 pages.

International Searching Authority, "Notification of Transmittal of International Preliminary Report on Patentability and International Preliminary Report on Patentability," PCT/US13/031813, dated Mar. 9, 2015, 18 pages.

* cited by examiner

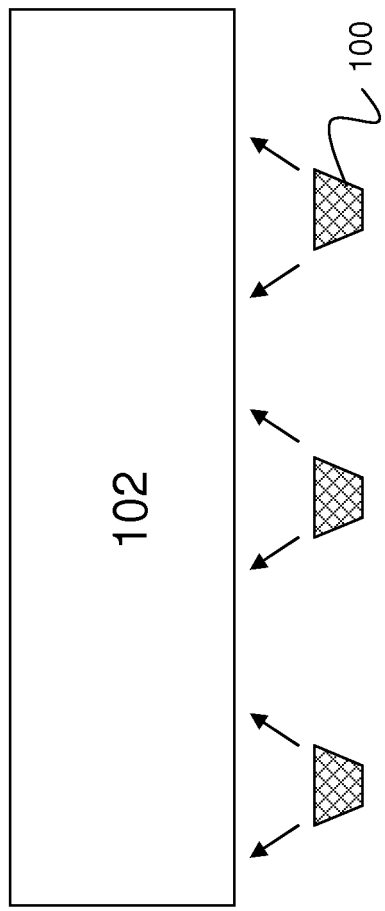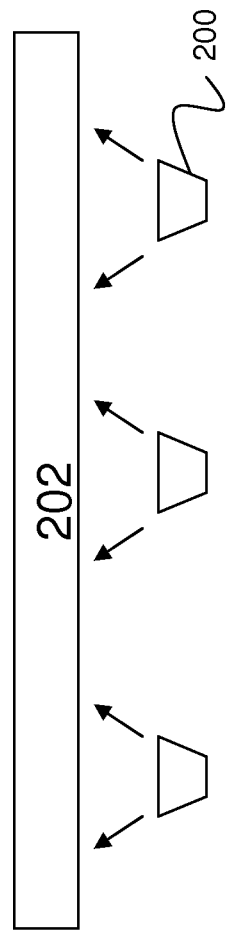

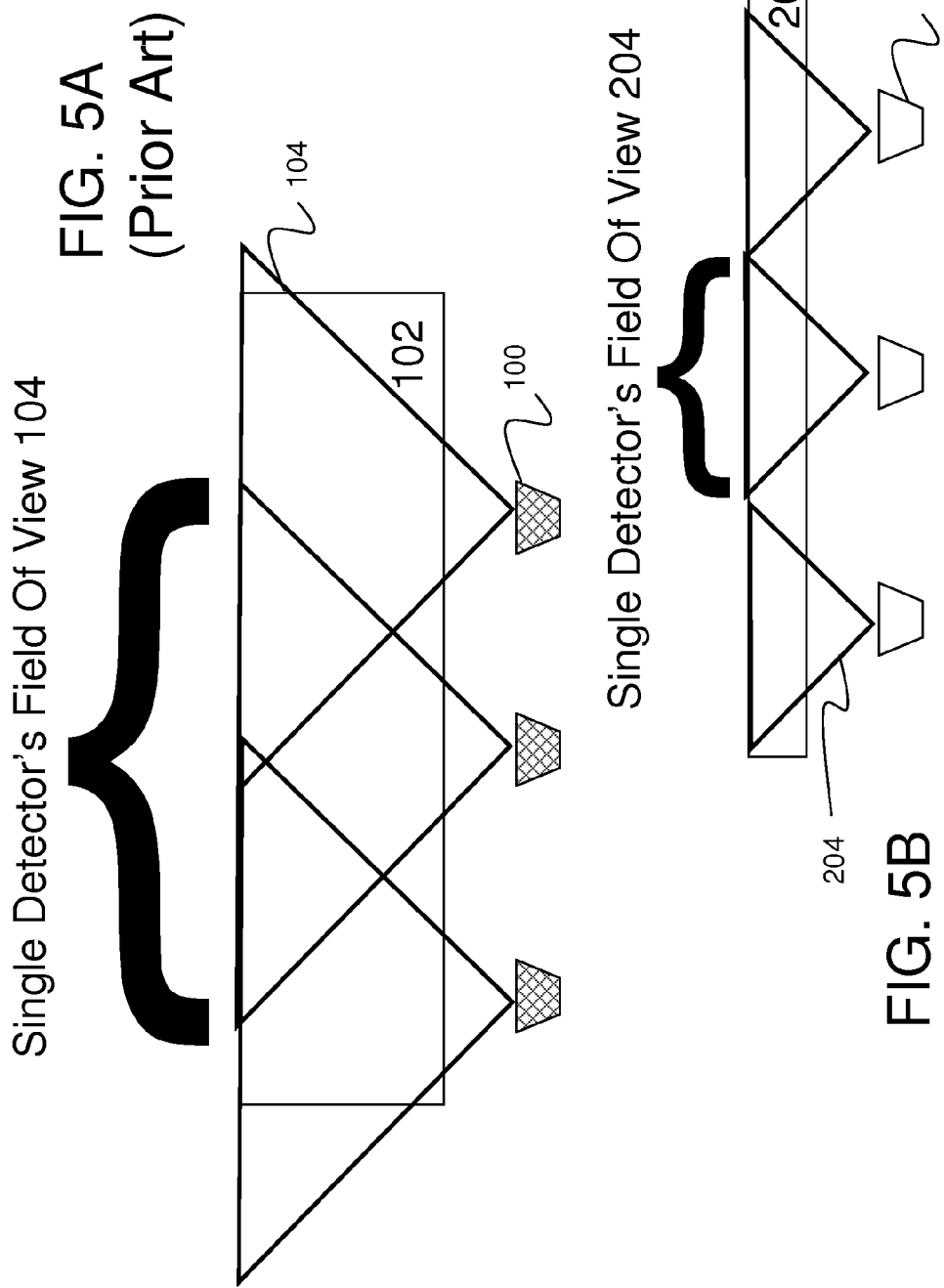

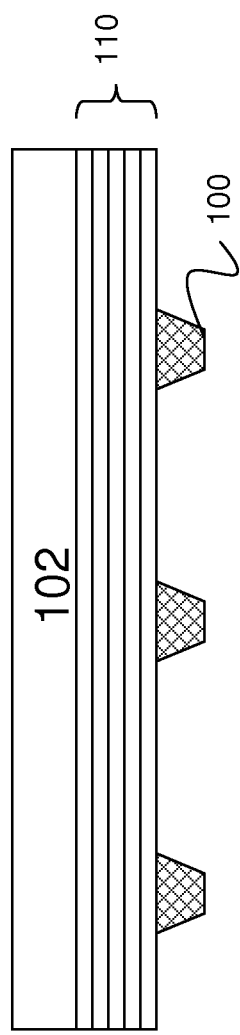
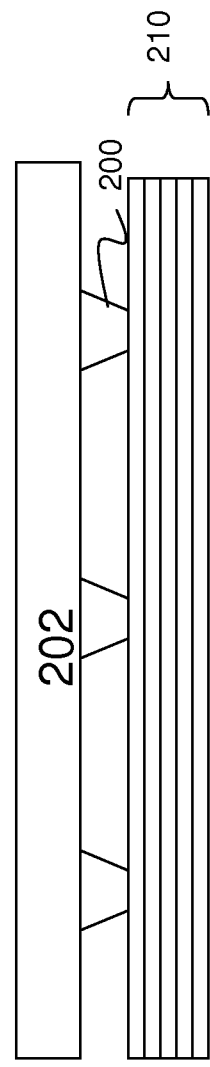

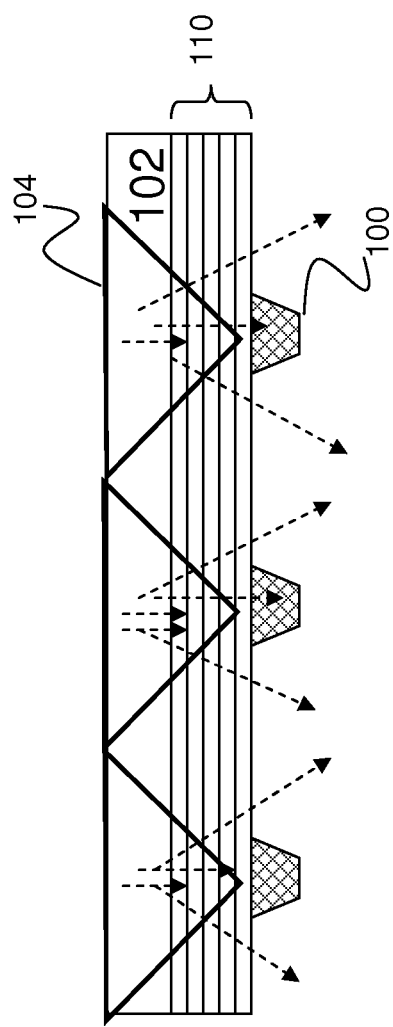
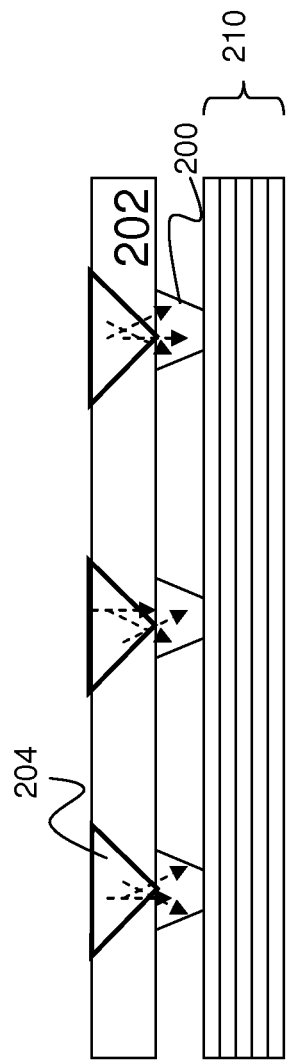

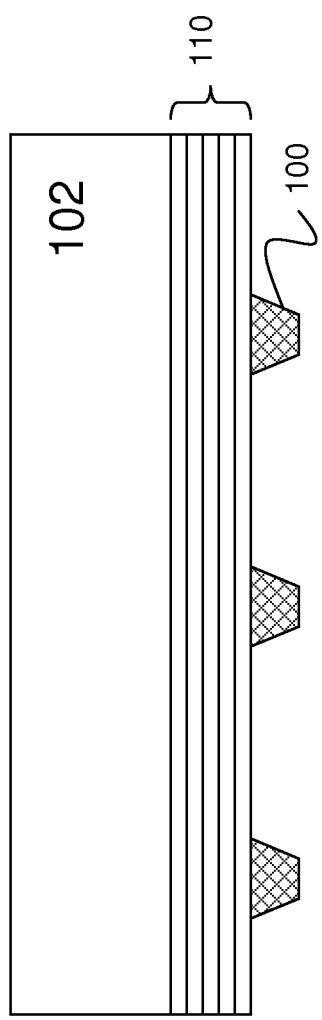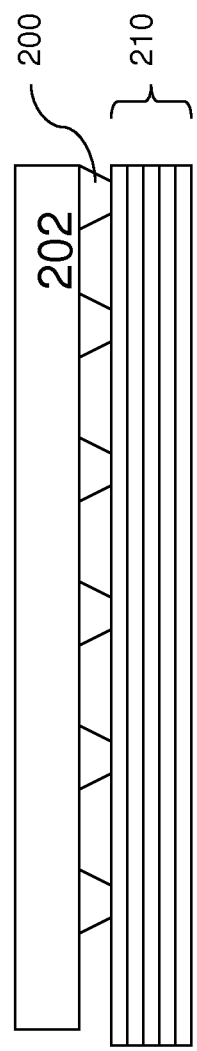

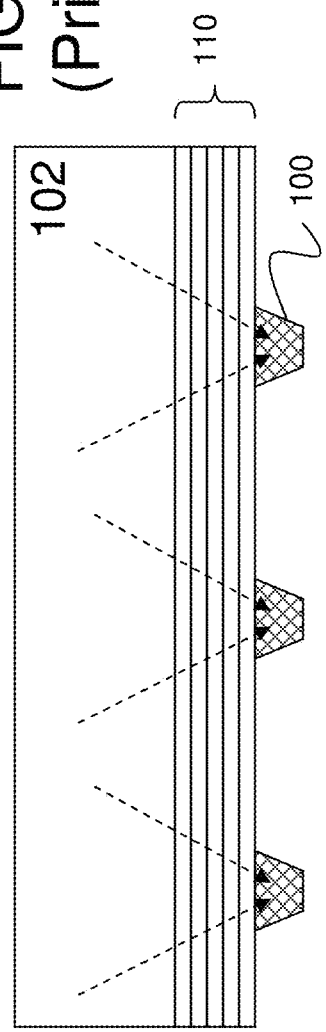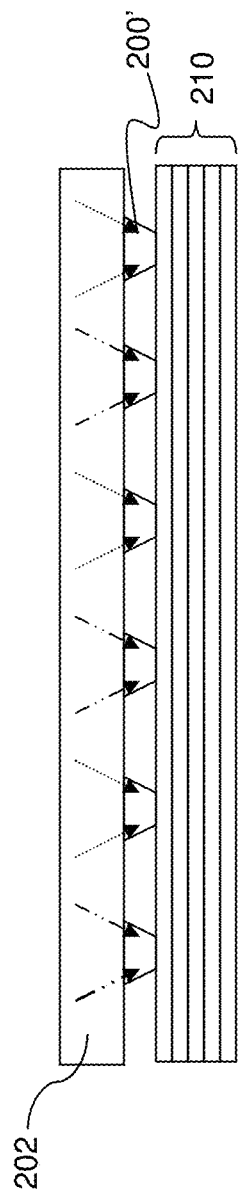

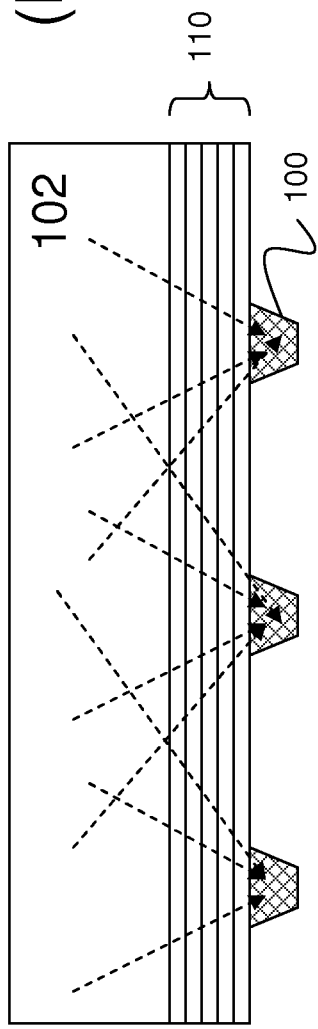
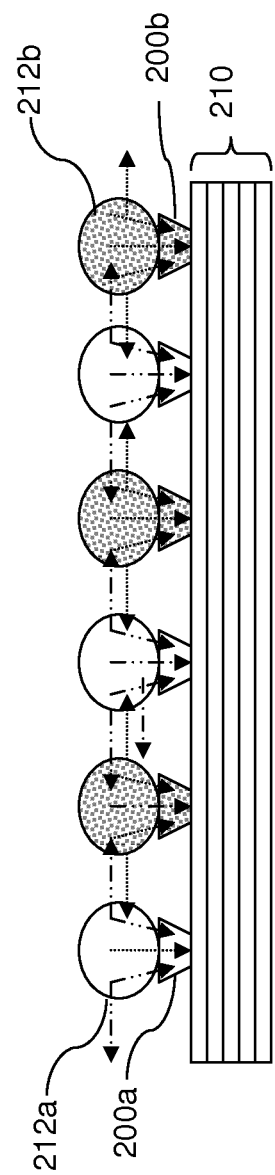

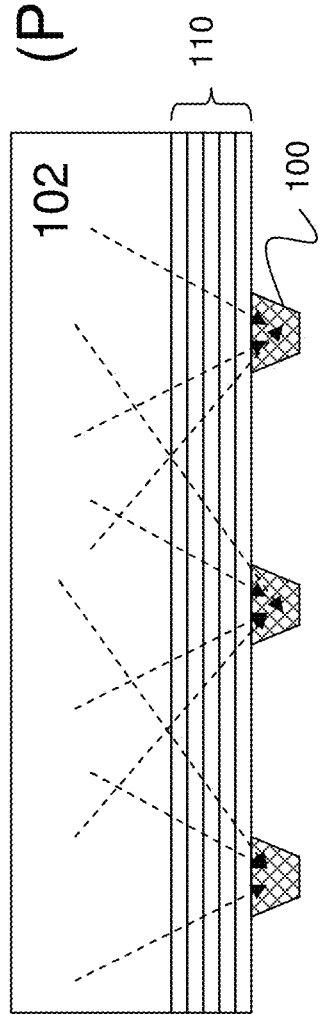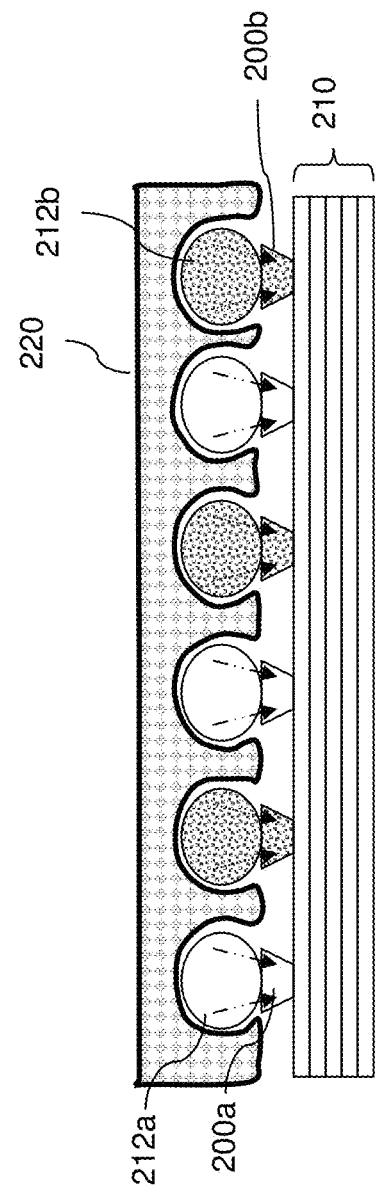

QUANTUM DOT DIGITAL RADIOGRAPHIC DETECTION SYSTEM

The present application is an application claiming the benefit of U.S. Provisional Patent Application Ser. No. 61/364,448, filed Jul. 15, 2010. The present application is based on and claims priority from this application, the disclosure of which is hereby expressly incorporated herein by reference in its entirety.

BACKGROUND OF INVENTION

Disclosed herein is a digital radiographic detection system and, more specifically, a quantum dot digital radiographic detection system.

Digital radiography ("DR" or "DX") is a form of X-ray imaging, where a semiconductor visible light detection device (e.g. digital X-ray sensors or imagers) is used instead of traditional photographic film. The semiconductor visible light detection device is used to record the X-ray image and make it available as a digital file that can be presented for interpretation and saved as part of a patient's medical record. U.S. Pat. No. 7,294,847 to Imai, U.S. Pat. No. 7,250,608 to Ozeki, and U.S. Pat. No. 5,017,782 to Nelson describe examples of digital radiographic detection devices (also referred to as "radiographic detectors") and related technology and are herein incorporated by reference. The disclosures of these references are herein incorporated by reference.

Advantages of digital radiography over traditional photographic film include, but are not limited to, the fact that digital radiography has the ability to digitally transfer images, the ability to digitally save images, the ability to digitally enhance images (e.g. the ability to apply special image processing techniques that enhance overall display of the image), the ability to use images that might otherwise have been insufficient (e.g. a wider dynamic range makes digital radiography more forgiving for over- and under-exposure), the ability to immediately have an image available for preview (e.g. time efficiency through bypassing chemical processing), the ability to use less radiation to produce an image of similar contrast to conventional radiography, and the ability to reduce costs (e.g. costs associated with processing film, managing film, and storing film).

Conventional digital radiographic detection devices (also referred to as "silicon-based light detection devices") currently use digital image capture technologies such as CCD (charge coupled device) and CMOS (complementary metal oxide semiconductor) image sensors (also referred to as "semiconductor visible light detectors" or "imagers") as the underlying semiconductor technologies. Both CCD and CMOS image sensors are silicon-based image sensors that require overlying scintillation layers for indirect conversion of X-rays into visible light. Both CCD and CMOS image sensors use light detectors to read the overlying scintillation layer. Both types of image sensors convert light into electric charge and process it into electronic signals. In a CCD image sensor, every pixel's charge is transferred through a very limited number of output nodes (often just one output node) to be converted to voltage, buffered, and sent off-chip as an analog signal. Because all of the pixels in the CCD sensor can be devoted to light capture, the CCD sensor has a high output uniformity (which generally results in better image quality). In a CMOS image sensor, each pixel has its own charge-to-voltage conversion so the CMOS image sensor has lower output uniformity than the output of the CCD image sensor. On the other hand, the CMOS image sensor can be built to require less off-chip circuitry for basic operation. The CMOS image sensor also includes additional functions such as amplifiers, noise-correction, and digitization circuits so that the CMOS image sensor chip outputs digital bits.

Conventional silicon-based image sensors (including CCD and CMOS) have been used for indirect conversion of ionizing X-radiation into visible images for medical and dental use. There are, however, inherent physical drawbacks to the use of CCD and CMOS sensors for X-radiography including, but not limited to the requirement of relatively thick scintillation layers, the requirement that detectors must be embedded within the physical body of the silicon device, the requirement of large individual detector sizes, low detector efficiency for capturing generated photons, low active sensor detection area/total detector size ratio, the inability to optimize peak sensor optical sensitivity to the scintillation chemistry, and the narrow practical dynamic range between over and under exposure by practitioner. These limitations result in a blurred image, low sensor image contrast, and a narrow dynamic range. A wide variety of techniques, including unique physical designs of the scintillation layer and software compensations, are required to minimize these limitations.

From a practitioner's perspective, direct digital radiographic detection devices that use CCD and CMOS image sensors have diagnostic qualities that are very poor as compared to direct digital radiographic detection devices that use traditional film. Digital radiographic detection devices that use CCD and CMOS image sensors have poor edge definition in the native image, poor contrast levels in the native image, very narrow dynamic range between over and under exposed images, and most of the photons generated by the scintillation layer (over 95%) are simply not detected. Without significant software enhancement CCD and CMOS images would not be diagnostic. The limitations are inherent to how CCD and CMOS image sensors function.

A quantum dot (fluorescent semiconductor nanocrystal) is a semiconductor whose excitations are confined in all three spatial dimensions. As a result, the quantum dots have properties that are between those of bulk semiconductors and those of discrete molecules. Simplistically, quantum dot detectors are semiconductors whose conducting characteristics are closely related to the size and shape of the individual crystal. Generally, the smaller the size of the crystal, the larger the band gap, the greater the difference in energy between the highest valence band and the lowest conduction band becomes, therefore more energy is needed to excite the dot, and concurrently, more energy is released when the crystal returns to its resting state. One of main advantages in using quantum dots is that because of the high level of control possible over the size of the crystals produced, it is possible to have very precise control over the conductive properties of the material and fine tune the peak sensitivity to the frequency being detected.

BRIEF SUMMARY OF THE INVENTION

Disclosed herein is a digital radiographic detection system and, more specifically, a quantum dot digital radiographic detection system.

A first preferred digital quantum dot radiographic detection system described herein includes: a scintillation subsystem and a semiconductor visible light detection subsystem. The scintillation subsystem converts X-ray ionizing radiation into luminescent visible light. The semiconductor visible light detection subsystem has a quantum dot semiconductor substrate and a plurality of quantum dot image sensors. The quantum dot image sensors detect the visible light from the scintillation subsystem and convert the visible light into at least one electronic signal. The plurality of quantum dot image sensors is in substantially direct contact with the scintillation subsystem. A first preferred digital quantum dot radiographic detection system may optionally have one or more of the following inventive features: the plurality of quantum dot image sensors being arranged in an array; the plurality of quantum dot image sensors being heterogeneous; the scintillation subsystem including a plurality of discrete scintillation packets (which may be heterogeneous), at least one of the discrete scintillation packets communicating with at least one of the quantum dot image sensors; an optically opaque layer being positioned between discrete scintillation packets; an optically opaque lateral layer with optical retroflectors positioned opposite the quantum dot image sensors.

A second preferred digital quantum dot radiographic detection system described herein includes: a scintillation subsystem and a semiconductor visible light detection subsystem. The scintillation subsystem converts X-ray ionizing radiation into luminescent visible light. The semiconductor visible light detection subsystem has a quantum dot semiconductor substrate and a plurality of quantum dot image sensors. The quantum dot image sensors detect the visible light from the scintillation subsystem and convert the visible light into at least one electronic signal. The scintillation subsystem is a plurality of discrete scintillation packets, at least one of the discrete scintillation packets communicating with at least one of the quantum dot image sensors. A second preferred digital quantum dot radiographic detection system may optionally have one or more of the following inventive features: the plurality of quantum dot image sensors being arranged in an array; the plurality of quantum dot image sensors being heterogeneous; the plurality of discrete scintillation packets may be heterogeneous; an optically opaque layer being positioned between discrete scintillation packets; an optically opaque lateral layer with optical retroflectors positioned opposite the quantum dot image sensors.

The subject matter of the present invention is particularly pointed out and distinctly claimed in the concluding portion of this specification. However, both the organization and method of operation, together with further advantages and objects thereof, may best be understood by reference to the following descriptions taken in connection with accompanying drawings wherein like reference characters refer to like elements.

BRIEF DESCRIPTION OF THE SEVERAL VIEWS OF THE DRAWINGS

The accompanying drawings illustrate various exemplary quantum dot digital radiographic detection systems and/or provide teachings by which the various exemplary quantum dot radiographic detection systems are more readily understood.

FIG. 4A is a simplified diagram showing the interaction between conventional image sensor arrays (including CCD or CMOS image sensors) and scintillation layers of conventional radiographic detection devices.

FIG. 4B is a simplified diagram showing exemplary interaction between quantum dot image sensor arrays and scintillation layers of exemplary preferred quantum dot radiographic detection systems.

FIG. 5A is a simplified diagram showing the fields of view of conventional image sensors with respect to the thickness of scintillation layers of conventional radiographic detection devices.

FIG. 5B is a simplified diagram showing exemplary fields of view of quantum dot image sensors with respect to the relative thickness of scintillation layers of exemplary preferred quantum dot radiographic detection systems.

FIG. 6A is a simplified diagram showing the placement of the conventional image sensors associated with the semiconductor substrate of conventional radiographic detection devices.

FIG. 6B is a simplified diagram showing exemplary placement of quantum dot image sensors associated with the semiconductor substrate of exemplary preferred quantum dot radiographic detection systems.

FIG. 7A is a simplified diagram showing the placement of conventional image sensors associated with the semiconductor substrate, the field of view of the image sensors with respect to the thickness of the scintillation layers, and the movement of scattered photons from the scintillation layers of conventional radiographic detection devices.

FIG. 7B is a simplified diagram showing exemplary placement of quantum dot image sensors associated with the semiconductor substrate, the field of view of the quantum dot image sensors with respect to the thickness of the scintillation layers, and the movement of scattered photons from the scintillation layers of exemplary preferred quantum dot radiographic detection systems.

FIG. 8A is a simplified diagram showing the density of conventional image sensor arrays (including CCD or CMOS image sensors) in conventional radiographic detection devices.

FIG. 8B is a simplified diagram showing exemplary density of quantum dot image sensor arrays in exemplary preferred quantum dot radiographic detection systems.

FIG. 10A is a simplified diagram showing placement of conventional image sensors associated with the semiconductor substrate of conventional radiographic detection devices.

FIG. 10B is a simplified diagram showing exemplary placement of optimized quantum dot image sensors associated with the semiconductor substrate of exemplary preferred quantum dot radiographic detection systems.

FIG. 12A is a simplified diagram showing conventional radiographic detection devices having optical "cross-talk" between conventional image sensors, the conventional image sensors associated with conventional scintillation layers.

FIG. 12B is a simplified diagram showing an exemplary preferred quantum dot radiographic detection system having reduced or eliminated optical "cross-talk" between quantum dot image sensors, each quantum dot image sensor associated with a discrete scintillation packet.

FIG. 13A is a simplified diagram showing conventional radiographic detection devices having optical "cross-talk" between conventional image sensors, the conventional image sensors associated with conventional scintillation layers.

FIG. 13B is a simplified diagram showing an exemplary preferred quantum dot radiographic detection system in which optical "cross-talk" between quantum dot image sensors is reduced or eliminated, each quantum dot image sensor is associated with a discrete scintillation packet and an optically opaque layer is positioned between the scintillation packets.

Figure 1:
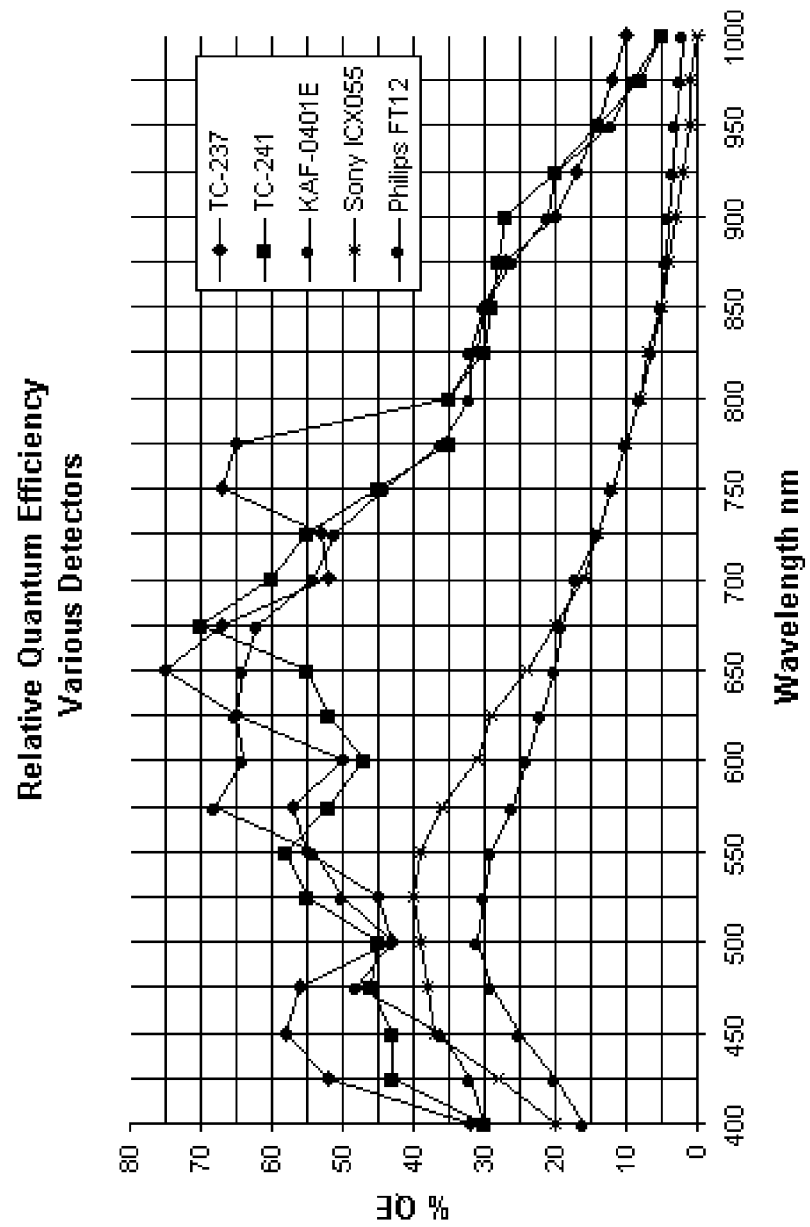
FIG. 1 is a graph showing the percentage quantum efficiency as a function of visible wavelength of light of various conventional image sensor arrays including CMOS and CCD visible light detectors.

The drawing figures are not necessarily to scale. Certain features or components herein may be shown in somewhat schematic form and some details of conventional elements may not be shown or described in the interest of clarity and conciseness. The drawing figures are hereby incorporated in and constitute a part of this specification.

DETAILED DESCRIPTION OF THE INVENTION

Disclosed herein is a digital radiographic detection system and, more specifically, a quantum dot digital radiographic detection system (also referred to as a "quantum dot radiographic detector"). Exemplary quantum dot radiographic detection systems may be better understood with reference to the drawings, but the shown and described quantum dot radiographic detection systems are not intended to be of a limiting nature.

The exemplary quantum dot radiographic detection systems described herein minimize most of the inherent limitations of CCD or CMOS conventional radiographic detection devices. For example, preferred digital quantum dot radiographic detection systems have an image quality sharp enough that edge detection software is not required, although additional image enhancement will be possible. Further, preferred digital quantum dot radiographic detection systems have higher contrast levels than conventional digital radiographic detection devices because the image is not obfuscated by thick scintillation layers. The use of preferred digital quantum dot radiographic detection systems preferably reduces patient X-ray exposure by approximately 25%-50% compared to convention radiographic detection devices. Still further, preferred quantum dot radiographic detection systems have the ability to optimize quantum efficiencies to match multiple scintillation chemistries for enhanced X-ray detection. Finally, preferred digital quantum dot radiographic detection systems have the ability to capture parallel images in real-time during single exposures to create the widest dynamic range of any sensor in order to eliminate over and under exposed images.

Before describing the quantum dot digital radiographic detection system, some of the terminology should be clarified. Please note that the terms and phrases may have additional definitions and/or examples throughout the specification. Where otherwise not specifically defined, words, phrases, and acronyms are given their ordinary meaning in the art.

"Digital radiographic detection devices or systems" are used by practitioners (i.e. any qualified user of radiographic detection devices or systems) to perform the process of receiving a radiation signal (such as X-rays), converting the radiation signal into visible light (or "light"), detecting the light as a plurality of images through the use of image sensors, converting the plurality of images into corresponding electronic signals, and digitally processing a plurality of electronic signals into a single coherent image. It should be noted that "light" for the purposes of this specification refers only to "visible light" (i.e. light within the visible spectrum, but not X-rays or infrared). In an exemplary quantum dot radiographic detection system, X-rays are used to generate useful diagnostic images. In order to produce these images, X-rays generated by an X-ray source, pass through the patient's body and eventually into a scintillation layer. The electrons in the scintillation material are excited by the ionizing radiation (i.e. X-rays), and emit visible light (by "luminescence") based in the scintillating material used. The visible light is then detected using the semiconductor visible light detection subsystem and converted into an electronic signal (similar to the process used in digital photography). The efficiency of the semiconductor visible light detection subsystem described herein may be dependent on the semiconductor substrate and corresponding circuitry used. The detected visible light can then be converted into an electronic signal that is suitable for storage and software manipulation to render the final diagnostic image.

"Quantum dot semiconductors" (also referred to as "quantum dots," "quantum dot detectors," and "fluorescent semiconductor nanocrystals") are semiconductors whose excitations are confined in all three spatial dimensions. As a result, the quantum dots have properties that are between those of bulk semiconductors and those of discrete molecules. The quantum dot radiographic detection system described herein uses quantum dots in combination with a scintillating medium to convert X-rays into visible light and substantially concurrently capture the visible light. Exemplary quantum dot semiconductors (quantum dot optical devices with enhanced gain and sensitivity and methods of making same) are described in U.S. Pat. No. 7,773,404 to Sargent et al. (the "Sargent reference"), the disclosure of which is herein incorporated by reference. On the other hand, U.S. Pat. No. 7,126,136 to Chen (the "Chen reference") describes using nanoparticles or quantum dots as exhibiting photostimulated luminescence ("PSL") for the storage of digital information. Put another way, the quantum dots described herein function as "detectors" whereas the quantum dots described in the Chen reference function as optical emitters, which are the opposite of detectors.

A "computational device," "computing system," "computer," "processing unit," and/or "processor" (referred to generically as "computational devices") are devices capable of executing instructions or steps and may be implemented as a programmable logic device or other type of programmable apparatus known or yet to be discovered. The computational devices may have associated memory. A computational device may be implemented as a single device or as a plurality of sub-devices.

The term "memory" is defined to include any type of computer (or other computational device)-readable media (also referred to as machine-readable storage medium) including, but not limited to attached storage media (e.g. hard disk drives, network disk drives, servers), internal storage media (e.g. RAM, ROM, EPROM, FLASH-EPROM, or any other memory chip or cartridge), removable storage media (e.g. CDs, DVDs, flash drives, memory cards, floppy disks, flexible disks), firmware, and/or other storage media known or yet to be discovered. Memory may be implemented as a single device or as a plurality of sub-memories.

It should be noted that the terms "programs" and "subprograms" are defined as a series of instructions that may be implemented as "software" (i.e. computer program instructions or computer-readable program code) that may be loaded onto a computer (or other computational device) to produce a machine, such that the instructions that execute on the computer create structures for implementing the functions described herein. Further, these programs and subprograms may be loaded onto a computer so that they can direct the computer to function in a particular manner, such that the instructions produce an article of manufacture including instruction structures that implement the functions described herein. The programs and subprograms may also be loaded onto a computer to cause a series of operational steps to be performed on or by the computer to produce a computer implemented process such that the instructions that execute on the computer provide steps for implementing the functions described herein. The phrase "loaded onto a computer" also includes being loaded into the memory of the computer or a memory associated with or accessible by the computer. The programs and subprograms may be divided into multiple modules or may be combined.

It should be noted that the terms "may," "might," "can," and "could" are used to indicate alternatives and optional features and only should be construed as a limitation if specifically included in the claims. It should be noted that the various components, features, steps, or embodiments thereof are all "preferred" whether or not it is specifically indicated. Claims not including a specific limitation should not be construed to include that limitation.

It should be noted that, unless otherwise specified, the term "or" is used in its nonexclusive form (e.g. "A or B" includes A, B, A and B, or any combination thereof, but it would not have to include all of these possibilities). It should be noted that, unless otherwise specified, "and/or" is used similarly (e.g. "A and/or B" includes A, B, A and B, or any combination thereof, but it would not have to include all of these possibilities). It should be noted that, unless otherwise specified, the terms "includes" and "has" mean "comprises" (e.g. a device that includes, has, or comprises A and B contains A and B, but optionally may contain C or additional components other than A and B). It should be noted that, unless otherwise specified, the singular forms "a," "an," and "the" refer to one or more than one, unless the context clearly dictates otherwise.

To perform the radiographic detection process, the exemplary digital radiographic detection systems described herein utilize various subsystems. The subsystems of exemplary radiographic detection system can be discussed as the "scintillation subsystem" (which can be a "scintillation layer" or a "scintillation packet"), the "semiconductor visible light detection subsystem," and the "image processing subsystem."

Preferred scintillation subsystems convert X-ray ionizing radiation into luminescent visible light. Conventional radiographic detection devices use scintillation layers made from a material suitable for converting X-ray radiation into visible light (a "scintillation layer"), such as by the use of a luminescent material. The luminescent material may be a conventional scintillation material (e.g. caesium iodine or gadolinium oxysulfide), or may be phosphor materials as described in the Chen reference. Generally, scintillation layers are capable of producing additional visible light in proportion to their thickness, but it is also well known that as the scintillation layer gets thicker the image becomes "blurred" and image contrast decreases. Alternative preferred scintillation subsystems, as discussed below, may be implemented as discrete scintillation packets.

One preferred semiconductor visible light detection subsystem includes a plurality of image sensors (also referred to as "semiconductor visible light detectors" or "imagers"). Image sensors detect the light generated by the scintillation subsystem and convert it into an electronic signal through the use of the semiconductor substrate. The semiconductor visible light detection subsystem of the quantum dot digital radiographic detection systems described herein includes quantum dot image sensors in the semiconductor substrate (the quantum dot semiconductor substrate). The semiconductor substrate includes the circuitry and material necessary for converting the detected visible light signal into a corresponding electronic signal. Due to a limited field of view for each individual image sensor, a single image sensor would be insufficient to capture an image of diagnostic value. Using an array of image sensors associated with the semiconductor substrate facilitates the image sensors, in aggregate, having a field of view sufficiently large enough to capture a useful diagnostic image (e.g. of a patient's jaw).

One preferred image processing subsystem includes a computational device (e.g. a computer with an associated image rendering program) that is capable of receiving electronic signals from the semiconductor visible light detection subsystem and digitally storing the electronic signals on an electronic medium as useful detection data. The computational device then uses imaging software to align the electronic signals from the individual image sensors to create a larger diagnostic image. The image processing subsystem also includes any suitable connector between the semiconductor visible light detection subsystem and the image processing device.

Figure 2:
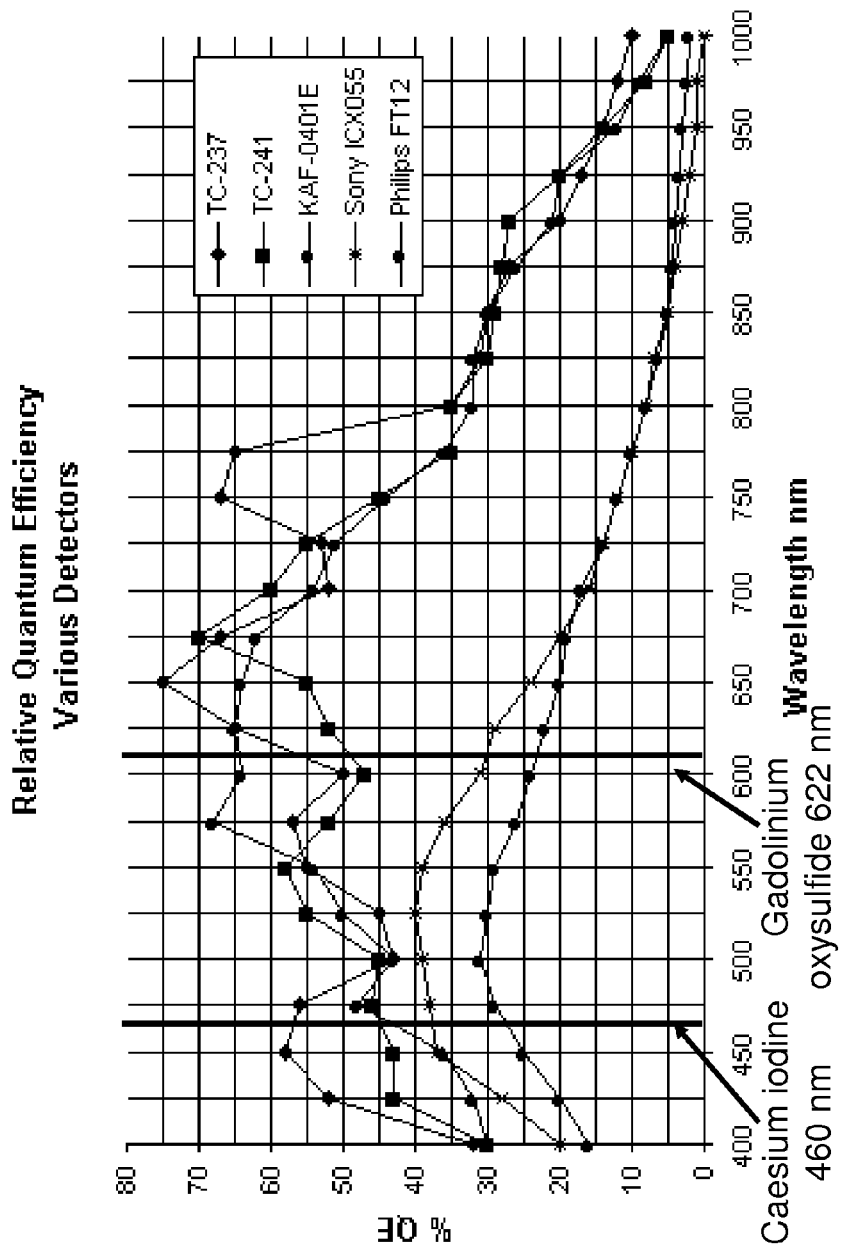
FIG. 2 is a graph showing the percentage quantum efficiency as a function of visible wavelength of light of various conventional image sensor arrays including CMOS and CCD visible light detectors (as shown in FIG. 1) and, additionally, the wavelengths of two common scintillation materials for converting ionizing x-radiation to visible light at the shown frequencies.
Figure 3:
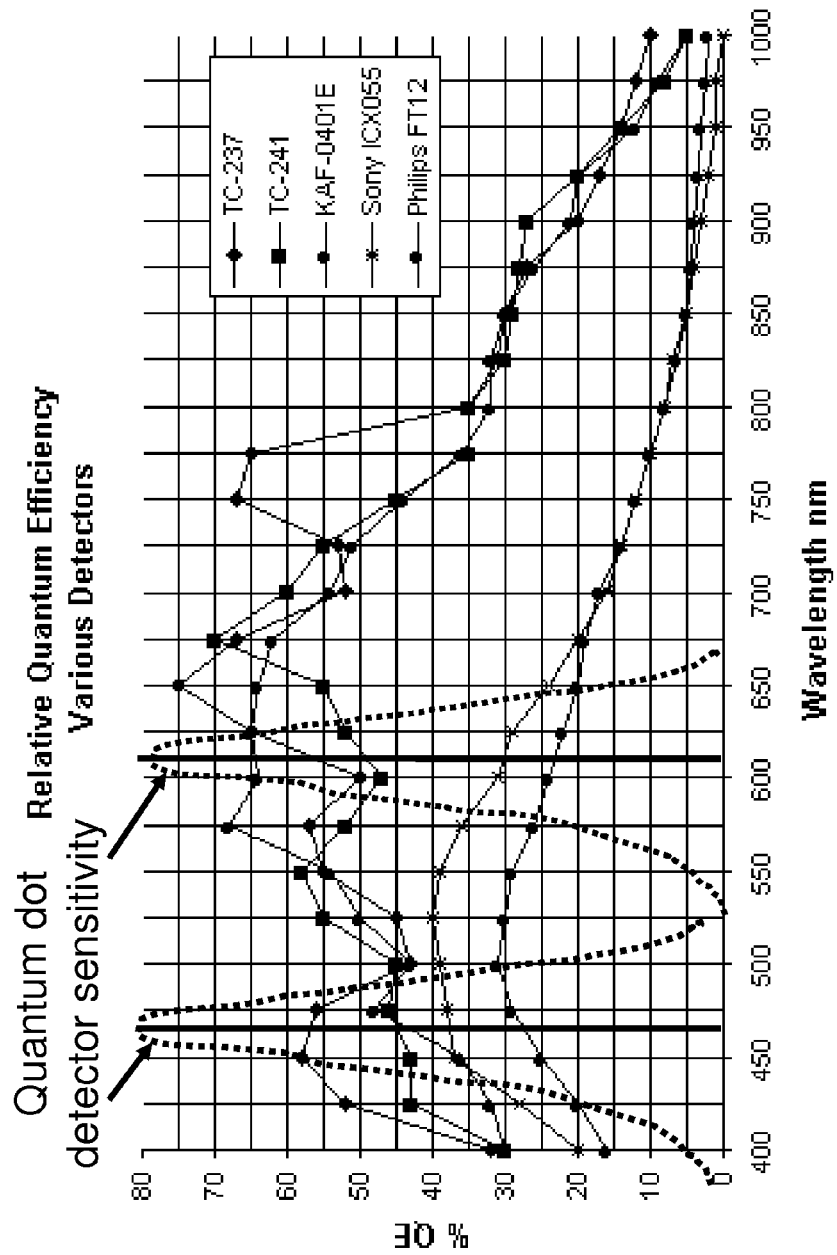
FIG. 3 is a graph similar to FIG. 2 showing, in addition, quantum dot detector sensitivities of the tuned visible light ranges.

FIGS. 1-3 are graphs pertaining to the scintillation subsystem and, in particular, the at least one scintillation layer.

FIG. 1 is a graph showing the quantum efficiency (as a percentage (% QE)) of various conventional digital optical detection systems (such as CMOS or CCD detectors) as a function of wavelength of light. It should be noted that although the % QE is very high at certain wavelengths, the luminescence of the scintillation material will generally control what wavelength of visible light the image sensor will receive. FIG. 2 shows the graph of FIG. 1 with the addition of the predominate wavelengths of two common scintillation materials: caesium iodide (460 nm) and gadolinium oxysulfide (622 nm). The graph shows the % QE at these wavelengths for the various conventional digital radiographic detection systems to be between 25% and 65%. Because of the static nature of the conductivity properties of the semiconductors in these conventional radiographic detection devices, the % QE cannot be improved at various wavelengths without changing the semiconductor substrate.

In contrast to the semiconductor substrate of the conventional digital radiographic detection system, a quantum dot semiconductor substrate can be "attenuated" (have its conductivity properties adjusted) based on the size and shape of the quantum dots. This allows for the production of semiconductor substrates that have high % QE at desirable wavelengths, such as the predominate wavelengths of the scintillation material. FIG. 3 shows the graph of FIG. 1 with the addition of quantum dot radiographic detection systems (shown as dotted lines) having semiconductor substrates with quantum dots attenuated for caesium iodide and gadolinium oxysulfide luminescence. It should be noted that the attenuation is dynamic, and if a different scintillation material was used, the quantum dot semiconductor substrate could be accordingly attenuated for high % QE.

FIGS. 4-14 are each divided into "A" and "B" depictions. The A depiction relates to conventional radiographic detection devices and the B depiction relates to quantum dot radiographic detection systems. For some features, multiple elements are only designated a single time. For example, an array of image sensors is designated by the same reference number as a single reference number.

FIG. 4A shows the interaction between conventional image sensor arrays (including CCD or CMOS image sensors 100) and scintillation layers 102 of conventional radiographic detection devices. FIG. 4B shows exemplary interaction between quantum dot image sensor arrays (including quantum dot image sensors 200) and scintillation layers 202 of exemplary preferred quantum dot radiographic detection systems. These figures show that because quantum dot arrays 200 are able to detect four to ten times more available photons generated by the scintillation layer 202, thinner scintillation layers 202 may be used with the quantum dot arrays 200. FIG. 4B shows exemplary scintillation subsystems and semiconductor visible light detection subsystems of both conventional and quantum dot digital radiographic detection systems. The scintillation layer 202 of the quantum dot digital radiography detection system is significantly thinner than the scintillation layers 102 of conventional digital radiographic detection systems due to the increased ability of the semiconductor visible light detection subsystem to detect photons emitted by the scintillation subsystem. By altering the size and shape of the quantum dots 200, the quantum dot radiographic detection system can detect between four and ten times as many free photons generated by conventional scintillation layers 102. This in turn requires less visible light from the scintillation layer 202 to generate a diagnostic image, and therefore makes thicker conventional scintillation layers 102 obsolete.

FIG. 5A shows the fields of view 104 of conventional image sensors 100 with respect to the thickness of scintillation layers 102 of conventional radiographic detection devices. FIG. 5B shows exemplary fields of view 204 of quantum dot image sensors 200 with respect to the thickness of scintillation layers 202 of exemplary preferred quantum dot radiographic detection systems. These figures show an additional benefit to the quantum dot radiographic detection system's use of thinner scintillation layers 202. In the conventional digital radiographic detection systems, the conventional image sensors' fields of view 104 are wide, causing significant overlap between image sensors 100 within the array. This overlap causes the resulting images to be less sharp (without the aid of expensive light collimation processes), and therefore of less diagnostic value to a practitioner. In contrast, the quantum dot image sensors 200 of the quantum dot radiographic detection system have much narrower fields of view 204. This narrow field of view allows the image sensors 200 to be more densely positioned within the array, resulting in both improved native image contrast and image sharpness.

FIG. 6A shows the placement of the conventional image sensors 100 below layers of the semiconductor substrate 110 of conventional radiographic detection devices. FIG. 6B shows exemplary placement of quantum dot image sensors 200 above or on the top layer of the semiconductor substrate 210 of exemplary preferred quantum dot radiographic detection systems. FIG. 7A shows the placement of conventional image sensors 100 associated with the semiconductor substrate 110, the field of view of the image sensors with respect to the thickness of the scintillation layers 102, and the movement of scattered photons from the scintillation layers 102 of conventional radiographic detection devices. FIG. 7B shows exemplary placement of quantum dot image sensors 200 associated with the semiconductor substrate 210, the field of view of the quantum dot image sensors with respect to the thickness of the scintillation layers 202, and the movement of scattered photons from the scintillation layers 202 of exemplary preferred quantum dot radiographic detection systems. As shown in these figures, the conventional image sensors 100 are positioned significantly lower (shown as 5-8 layers into the semiconductor substrate 110) as compared to quantum dot image sensors 200 that are closer to or on the surface for "direct" contact with scintillation layers 202. It should be noted the term "direct" and the phrase "substantially direct" would not preclude the inclusion of an adhesive or other de minimus attachment layer or gap between the quantum dot image sensors 200 and the scintillation layers 202. Because the conventional image sensors 100 of conventional radiographic detection devices are located below several layers of the semiconductor substrate 110, there is an undesirably large distance between the scintillation layer 102 and the image sensors 100. This distance can lead to lost photons due to spatial defocusing, scattering, and absorption by the semiconductor substrate 110. In contrast, the quantum dot radiographic detection system allows the quantum dot image sensors 200 to be positioned in direct contact with (or substantially close to) the surface of the scintillation layer 202. This positioning allows the practitioner to obtain a superior quality image by eliminating or minimizing the loss of photons from the interference of the semiconductor substrate 210.

Figure 9A:
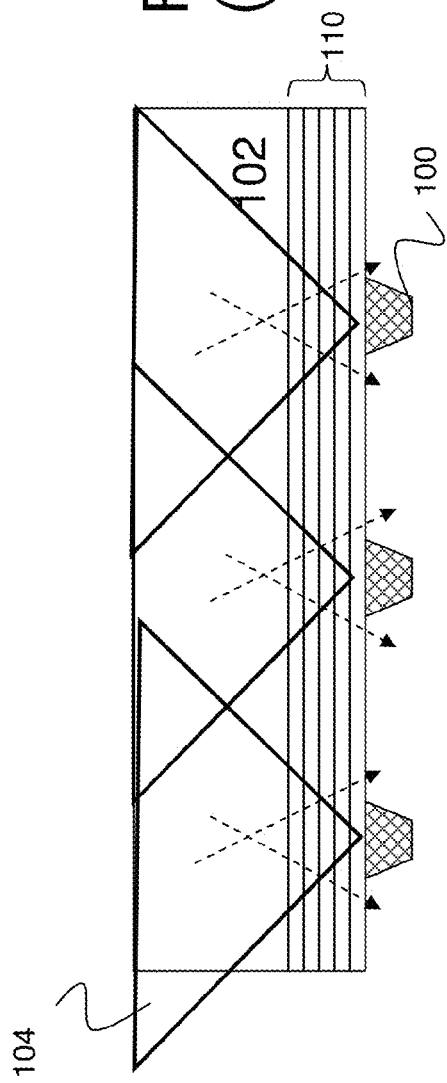
FIG. 9A is a simplified diagram showing density of conventional image sensor arrays (including CCD or CMOS image sensors), the field of view of conventional image sensors with respect to the thickness of the scintillation layers, and the movement of scattered photons from the scintillation layers in conventional radiographic detection devices.
Figure 9B:
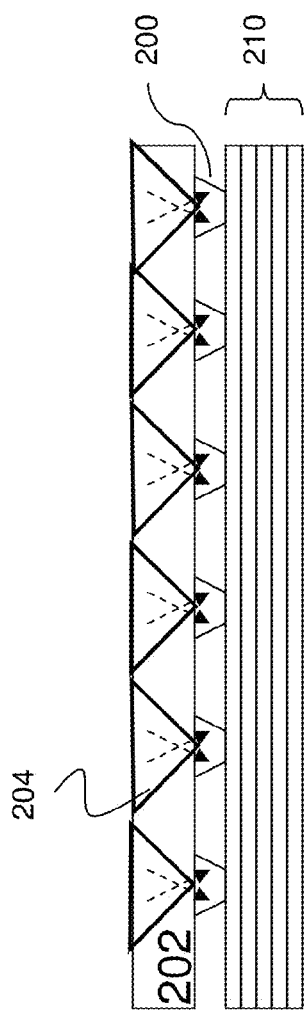
FIG. 9B is a simplified diagram showing exemplary density of quantum dot image sensor arrays, the field of view of quantum dot image sensors with respect to the thickness of the scintillation layers, and the movement of scattered photons from the scintillation layers in exemplary preferred quantum dot radiographic detection systems.

FIG. 8A shows the density of conventional image sensor arrays (including CCD or CMOS image sensors 100) in conventional radiographic detection devices. FIG. 8B shows exemplary density of quantum dot image sensor arrays (including quantum dot image sensors 200) in exemplary preferred quantum dot radiographic detection systems. FIG. 9A shows density of conventional image sensor arrays (including CCD or CMOS image sensors 100), the field of view of conventional image sensors with respect to the thickness of the scintillation layers 102, and the movement of scattered photons from the scintillation layers 102 in conventional radiographic detection devices. FIG. 9B shows exemplary density of quantum dot image sensor arrays (including quantum dot image sensors 200), the field of view of quantum dot image sensors with respect to the thickness of the scintillation layers 202, and the movement of scattered photons from the scintillation layers 202 in exemplary preferred quantum dot radiographic detection systems. These figures show the relative size limitations of both the conventional and quantum dot radiographic detection systems. In the conventional radiographic detection devices, the combination of the thick scintillation layer 102 and the position of the image sensors 100 below layers of the semiconductor substrate 110 significantly contribute to the image sensors' wide field of view 104 (FIG. 9A). These inherent qualities of the conventional radiographic detection devices makes increasing the density of image sensor array 100 impracticable, as it would simply increase the field of view overlap. In contrast, FIG. 9B shows that quantum dot radiographic detection systems are inherently capable of having a higher image sensor array density without causing the image sensors' fields of view 204 to overlap. Higher detector densities results in dramatically higher native image contrast and resolution along with the ability to detect more photons.

As shown in FIGS. 1-3, conventional image sensors 100 have a broadband response, but not high quantum efficiency. The various scintillation chemistries have a narrow band output. Quantum dot image sensors 200 can be tuned (e.g. optimized) to the peak outputs of these scintillation chemistries. Comparing FIG. 10A with FIG. 10B shows the advantage of this ability to tune/optimize the quantum dot image sensors 200. FIG. 10A shows placement of conventional image sensors 100 having nonlinear broadband frequency responses. FIG. 10B shows exemplary placement of optimized quantum dot image sensors 200' associated with the semiconductor substrate 210 of exemplary preferred quantum dot radiographic detection systems. The optimized quantum dot image sensors 200' are preferably tuned to the peak output of the scintillation layer 202. Optimization permits the specific scintillation chemistry to be used for greater conversion of available photons into useable data.

Figure 11A:
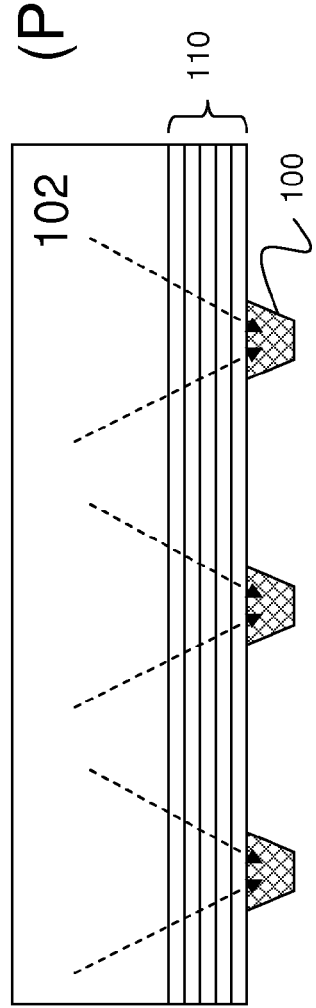
FIG. 11A is a simplified diagram showing conventional scintillation layers, conventional image sensors, and conventional semiconductor substrates of conventional radiographic detection devices.
Figure 11B:
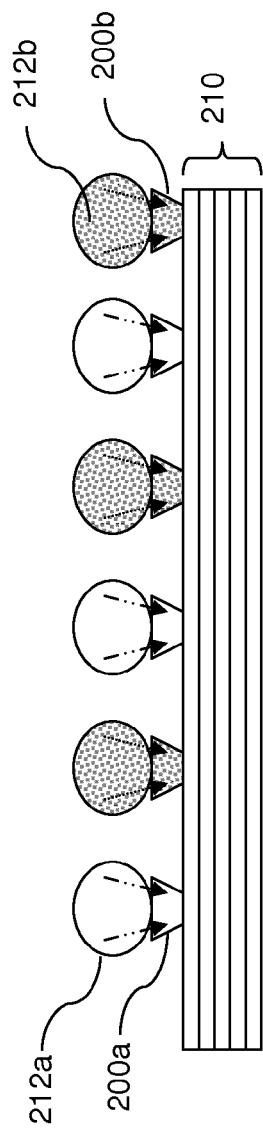
FIG. 11B is a simplified diagram showing quantum dot image sensors each associated with a discrete scintillation packet in exemplary preferred quantum dot radiographic detection systems.

FIG. 11A shows conventional scintillation layers 102, conventional image sensors 100, and conventional semiconductor substrates 110 of conventional radiographic detection devices. FIG. 11B shows quantum dot image sensors 200 (shown as 200a, 200b) each associated with a discrete scintillation packet 212 (shown as 212a, 212b) in exemplary preferred quantum dot radiographic detection systems. In this alternative quantum dot radiographic detection system, the scintillation subsystem includes discrete scintillation packets 212 instead of an overlying scintillation layer 102. These figures show individual scintillation packets 212 associated with individual quantum dot image sensors 200 on a one-to-one basis, although alternative scintillation packet-to-image sensor ratios may be used. The use of separated scintillation packets 212 in lieu of a uniform scintillation layer 102 allows the quantum dot radiographic detection system to be further attenuated by the use of more than one scintillation material. For example, the array of quantum dot image sensors 200 optionally may be heterogeneous (shown graphically as 200a, 200b) with respect to the optimum % QE, with 50% of the image sensors 200a being attenuated for maximum quantum efficiency at 460 nm, and 50% of the image sensors 200b being attenuated for maximum quantum efficiency at 622 nm. The scintillation packets 212 (shown graphically as 212a, 212b) may be similarly heterogeneous and associated with the appropriate (designed together to provide the correct results) quantum dot image sensors 200a, 200b based on the scintillation material, having caesium iodide scintillation packets 212a associated with the 460 nm image sensors 200a, and having the gadolinium oxysulfide scintillation packets 212b associated with the 622 nm image sensors 200b. The resulting images are derived from two separate scintillation materials, and the resulting images have higher resolution and contrast, resulting in greater diagnostic value.

FIGS. 12A and 13A show conventional radiographic detection devices having optical "cross-talk" between conventional image sensors 100, the conventional image sensors 100 associated with conventional scintillation layers 102. FIG. 12B shows an exemplary preferred quantum dot radiographic detection system having optical "cross-talk" between quantum dot image sensors 200, each quantum dot image sensor 200 associated with a discrete scintillation packet 212. Optical "cross-talk" in the scintillation layer loses photons and diminishes image contrast and sharpness as viewed by the optical detectors. As shown in FIG. 13A, optical "cross-talk" between conventional image sensors 100 cannot be eliminated because of the presence of the conventional scintillation layer 102. On the other hand, FIG. 13B shows an exemplary preferred quantum dot radiographic detection system in which optical "cross-talk" between quantum dot image sensors 200 is reduced or eliminated by adding an optically opaque layer 220 positioned between the scintillation packets 212.

Figure 14A:
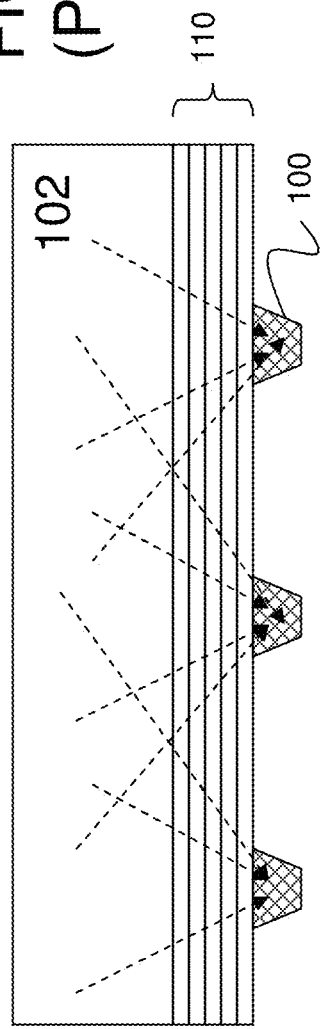
FIG. 14A is a simplified diagram showing conventional radiographic detection devices having optical "cross-talk" between conventional image sensors, the conventional image sensors associated with conventional scintillation layers.
Figure 14B:
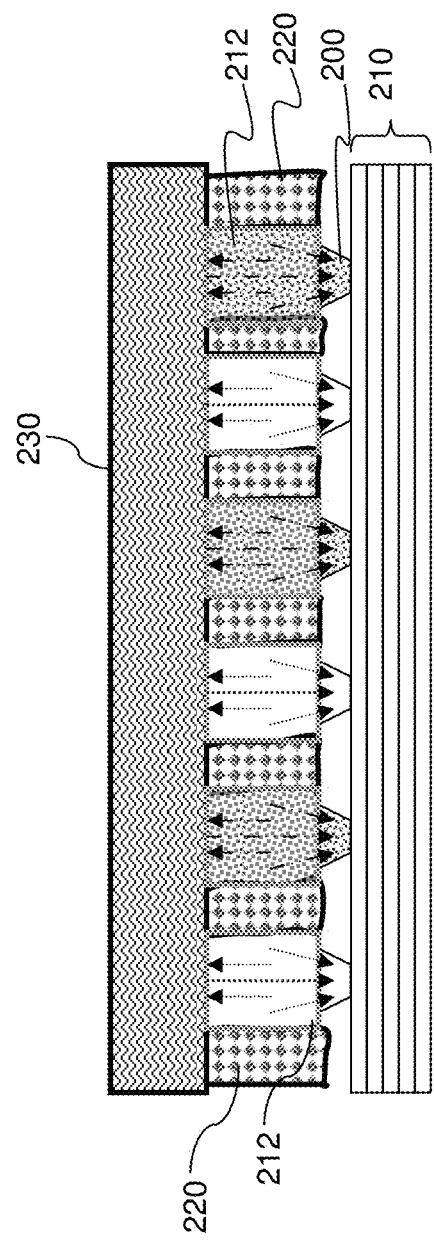
FIG. 14B is a simplified diagram showing an exemplary preferred quantum dot radiographic detection system in which optical "cross-talk" between quantum dot image sensors is reduced or eliminated, each quantum dot image sensor associated with a discrete scintillation packet, an optically opaque layer is positioned between the scintillation packets, and an optically opaque lateral layer with optical retroflectors is positioned opposite the quantum dot image sensors.

FIG. 14A shows conventional radiographic detection devices having optical "cross-talk" between conventional image sensors 100, the conventional image sensors 100 associated with conventional scintillation layers 102. FIG. 14B shows an exemplary preferred quantum dot radiographic detection system in which optical "cross-talk" between quantum dot image sensors 200 is reduced or eliminated using an optically opaque layer 220 positioned between the scintillation packets 212. FIG. 14B also shows the use of an optically opaque lateral layer 220 with optical retroflectors 230 positioned opposite the quantum dot image sensors 200. Put another way, the scintillation packets 212 are sandwiched between the opaque lateral layer 220 with optical retroflectors 230 and the quantum dot image sensors 200. The optically opaque lateral layer 220 with optical retroflectors 230 increases optical gain by reflecting scattered photons toward the quantum dot image sensors 200.

Alternative embodiments incorporating various elements described above are contemplated. For example, although shown as having heterogeneous quantum dot image sensors 200a, 200b, homogeneous quantum dot image sensors 200 could be used in the embodiments of FIGS. 11B, 12B, 13B, and/or 14B. Another example is that the optically opaque lateral layer 220 with optical retroflectors 230 shown in FIG. 14B could be used without the optically opaque layer positioned between the scintillation packets 212. A single discrete scintillation packet 212 may communicate with a plurality of quantum dot image sensors 200. A plurality of discrete scintillation packets 212 may communicate with a single quantum dot image sensor 200.

Cross-talk eliminating systems that eliminate optical cross-talk between image sensors and scintillation layers in conventional radiographic detection devices can also be used with the quantum dot radiographic detection systems described above. These conventional cross-talk eliminating systems generally consist of a collimated plate consisting of aligned fiber optics (having fibers that are glued, cut, and polished). Problems with conventional cross-talk eliminating systems include, but are not limited to their thickness, their delicateness, and their expensiveness. Accordingly, systems such as those described above that eliminate cross-talk in other ways would be extremely valuable.

It is to be understood that the inventions, examples, and embodiments described herein are not limited to particularly exemplified materials, methods, and/or structures. Further, all foreign and/or domestic publications, patents, and patent applications cited herein, whether supra or infra, are hereby incorporated by reference in their entirety.

The terms and expressions that have been employed in the foregoing specification are used as terms of description and not of limitation, and are not intended to exclude equivalents of the features shown and described. While the above is a complete description of selected embodiments of the present invention, it is possible to practice the invention using various alternatives, modifications, adaptations, variations, and/or combinations and their equivalents. It will be appreciated by those of ordinary skill in the art that any arrangement that is calculated to achieve the same purpose may be substituted for the specific embodiment shown. It is also to be understood that the following claims are intended to cover all of the generic and specific features of the invention herein described and all statements of the scope of the invention which, as a matter of language, might be said to fall therebetween.

What is claimed is:

1. A digital quantum dot radiographic detection system comprising:
    (a) a scintillation subsystem that converts X-ray ionizing radiation into luminescent visible light;
    (b) a semiconductor visible light detection subsystem having a semiconductor substrate and a plurality of quantum dot image sensors, said quantum dot image sensors detecting said visible light from said scintillation subsystem and converting said visible light into at least one electronic signal; and
    (c) said plurality of quantum dot image sensors is in substantially direct contact with said scintillation subsystem.

2. The system of claim 1 wherein said plurality of quantum dot image sensors are arranged in an array.

3. The system of claim 1 wherein said plurality of quantum dot image sensors are heterogeneous.

4. The system of claim 1 wherein said scintillation subsystem comprises a plurality of discrete scintillation packets, at least one of said discrete scintillation packets communicating with at least one of said quantum dot image sensors.

5. The system of claim 1 wherein said scintillation subsystem comprises a plurality of discrete scintillation packets, said plurality of quantum dot image sensors and said plurality of discrete scintillation packets being heterogeneous, at least one of said discrete scintillation packets communicating with an appropriate at least one of said quantum dot image sensors.

6. The system of claim 1 wherein said scintillation subsystem comprises a plurality of discrete scintillation packets, at least one of said discrete scintillation packets communicating with at least one of said quantum dot image sensors, and an optically opaque layer being positioned between said discrete scintillation packets.

7. The system of claim 1 wherein said scintillation subsystem comprises a plurality of discrete scintillation packets, said plurality of quantum dot image sensors and said plurality of discrete scintillation packets being heterogeneous, at least one of said discrete scintillation packets communicating with an appropriate at least one of said quantum dot image sensors, and an optically opaque layer being positioned between said discrete scintillation packets.

8. The system of claim 1 wherein said scintillation subsystem comprises a plurality of discrete scintillation packets, at least one of said discrete scintillation packets communicating with at least one of said quantum dot image sensors, and an optically opaque lateral layer with optical retroflectors positioned opposite said quantum dot image sensors.

9. The system of claim 1 wherein said scintillation subsystem comprises a plurality of discrete scintillation packets, said plurality of quantum dot image sensors and said plurality of discrete scintillation packets being heterogeneous, at least one of said discrete scintillation packets communicating with an appropriate at least one of said quantum dot image sensors, and an optically opaque lateral layer with optical retroflectors positioned opposite said quantum dot image sensors.

10. The system of claim 1 wherein said scintillation subsystem comprises a plurality of discrete scintillation packets, at least one of said discrete scintillation packets communicating with at least one of said quantum dot image sensors, an optically opaque layer being positioned between said discrete scintillation packets, and an optically opaque lateral layer with optical retroflectors positioned opposite said quantum dot image sensors.

11. The system of claim 1 wherein said scintillation subsystem comprises a plurality of discrete scintillation packets, said plurality of quantum dot image sensors and said plurality of discrete scintillation packets being heterogeneous, at least one of said discrete scintillation packets communicating with an appropriate at least one of said quantum dot image sensors, an optically opaque layer being positioned between said discrete scintillation packets, and an optically opaque lateral layer with optical retroflectors positioned opposite said quantum dot image sensors.

12. The system of claim 1 wherein said scintillation subsystem is positioned between an X-ray source and said plurality of quantum dot image sensors.

13. The system of claim 1 further comprising:
    (a) an image processing subsystem having a computational device capable of receiving said at least one electronic signal and storing said at least one electronic signal on an electronic medium; and
    (b) said computational device capable of retrieving and displaying said at least one electronic signal at a concurrent or later time as a diagnostic image.

14. A digital quantum dot radiographic detection system comprising:
    (a) a scintillation subsystem that converts X-ray ionizing radiation into luminescent visible light;
    (b) a semiconductor visible light detection subsystem having a semiconductor substrate and a plurality of quantum dot image sensors, said quantum dot image sensors detecting said visible light from said scintillation subsystem and converting said visible light into at least one electronic signal; and
    (c) said scintillation subsystem being a plurality of discrete scintillation packets, at least one of said discrete scintillation packets communicating with at least one of said quantum dot image sensors.

15. The system of claim 14 wherein said plurality of quantum dot image sensors are arranged in an array.

16. The system of claim 14 wherein said plurality of quantum dot image sensors are heterogeneous.

17. The system of claim 14 wherein said plurality of quantum dot image sensors and said plurality of discrete scintillation packets are heterogeneous, at least one of said discrete scintillation packets communicating with an appropriate at least one of said quantum dot image sensors.

18. The system of claim 14 further comprising an optically opaque layer being positioned between said discrete scintillation packets.

19. The system of claim 14 further comprising an optically opaque lateral layer with optical retroflectors positioned opposite said quantum dot image sensors.

20. The system of claim 14 further comprising an optically opaque layer being positioned between said discrete scintillation packets and an optically opaque lateral layer with optical retroflectors positioned opposite said quantum dot image sensors.

21. The system of claim 1 wherein said semiconductor substrate is a quantum dot semiconductor substrate.

22. The system of claim 14 wherein said semiconductor substrate is a quantum dot semiconductor substrate.

23. The system of claim 1 wherein said plurality of quantum dot image sensors are heterogeneous in that there are a plurality of different types of quantum dot image sensors.

24. The system of claim 1, said scintillation subsystem comprising a plurality of discrete scintillation packets, at least one of said discrete scintillation packets being in substantially direct contact with and in communication with an associated at least one of said quantum dot image sensors.

25. The system of claim 1, said scintillation subsystem comprising a plurality of discrete scintillation packets, at least one of said discrete scintillation packets in substantially direct contact with and in communication with an associated at least one of said quantum dot image sensors, each said quantum dot image sensor being optimized to a peak output of a scintillation chemistry of its associated discrete scintillation packet.

26. The system of claim 1, said scintillation subsystem comprising a plurality of discrete scintillation packets, at least one of said discrete scintillation packets in substantially direct contact with and in communication with an associated at least one of said quantum dot image sensors, each said quantum dot image sensor being optimized to a peak output of a scintillation chemistry of its associated discrete scintillation packet, wherein different types of optimized quantum dot image sensor and associated discrete scintillation packet combinations provide images having a high resolution and contrast.

27. The system of claim 14 wherein said plurality of quantum dot image sensors are heterogeneous in that there are a plurality of different types of quantum dot image sensors.

28. The system of claim 14, at least one of said discrete scintillation packets being in substantially direct contact with and in communication with an associated at least one of said quantum dot image sensors.

29. The system of claim 14, each said quantum dot image sensor being optimized to a peak output of a scintillation chemistry of its associated discrete scintillation packet.

30. The system of claim 14, each said quantum dot image sensor being optimized to a peak output of a scintillation chemistry of its associated discrete scintillation packet, wherein different types of optimized quantum dot image sensor and associated discrete scintillation packet combinations provide images having a high resolution and contrast.

31. A digital quantum dot radiographic detection system comprising:
(a) a scintillation subsystem that converts X-ray ionizing radiation into luminescent visible light;
(b) a semiconductor visible light detection subsystem having a semiconductor substrate and a plurality of quantum dot image sensors, said quantum dot image sensors detecting said visible light from said scintillation subsystem and converting said visible light into at least one electronic signal; and
(c) said scintillation subsystem being a plurality of discrete scintillation packets, at least one of said discrete scintillation packets in substantially direct contact with and communicating with at least one of said quantum dot image sensors, each said quantum dot image sensor being optimized to a peak output of a scintillation chemistry of its associated discrete scintillation packet.

* * * * *